United States Patent
Jang et al.

(10) Patent No.: US 11,911,184 B2
(45) Date of Patent: Feb. 27, 2024

(54) BIO-SIGNAL QUALITY ASSESSMENT APPARATUS AND BIO-SIGNAL QUALITY ASSESSMENT METHOD

(71) Applicant: SAMSUNG ELECTRONICS CO., LTD., Suwon-si (KR)

(72) Inventors: Dae Geun Jang, Yongin-si (KR); Ui Kun Kwon, Hwaseong-si (KR); Seung Keun Yoon, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 17/940,678

(22) Filed: Sep. 8, 2022

(65) Prior Publication Data

US 2023/0000444 A1 Jan. 5, 2023

Related U.S. Application Data

(63) Continuation of application No. 16/200,141, filed on Nov. 26, 2018, now Pat. No. 11,457,872.

(30) Foreign Application Priority Data

Dec. 1, 2017 (KR) .......... 10-2017-0164562
Jul. 2, 2018 (KR) .......... 10-2018-0076515

(51) Int. Cl.
*A61B 5/00* (2006.01)
*G16H 40/63* (2018.01)
(Continued)

(52) U.S. Cl.
CPC .......... *A61B 5/7221* (2013.01); *A61B 5/0205* (2013.01); *A61B 5/7246* (2013.01);
(Continued)

(58) Field of Classification Search
CPC ... A61B 5/7221; A61B 5/0205; A61B 5/7246; A61B 5/02405; A61B 5/02416;
(Continued)

(56) References Cited

U.S. PATENT DOCUMENTS 6,280,381 B1 8/2001 Malin et al.
6,405,065 B1 6/2002 Malin et al.
(Continued)

FOREIGN PATENT DOCUMENTS

EP 3 403 575 A1 11/2018
EP 3403574 A1 11/2018
(Continued)

OTHER PUBLICATIONS

Communication dated Oct. 9, 2022, issued by the National Intellectual Property Administration, PRC in counterpart Chinese Application No. 201811445058.1.
(Continued)

*Primary Examiner* — Ryan W Sherwin
(74) *Attorney, Agent, or Firm* — Sughrue Mion, PLLC

(57) ABSTRACT

A bio-signal quality assessment apparatus may include: a bio-signal obtainer configured to obtain a bio-signal; and a processor configured to extract periodic signals from the obtained bio-signal, and determine a signal quality index based on at least one of similarity between the extracted periodic signals and signal variability of the obtained bio-signal.

15 Claims, 10 Drawing Sheets

SIGNAL ANALYSIS PERIOD

(51) Int. Cl.
  *A61B 5/0205* (2006.01)
  *A61B 5/35* (2021.01)
  *A61B 5/024* (2006.01)
  *A61B 5/11* (2006.01)
  *A61B 7/04* (2006.01)

(52) U.S. Cl.
  CPC .......... *G16H 40/63* (2018.01); *A61B 5/02405* (2013.01); *A61B 5/02416* (2013.01); *A61B 5/1102* (2013.01); *A61B 5/35* (2021.01); *A61B 7/04* (2013.01)

(58) Field of Classification Search
  CPC ........... A61B 5/1102; A61B 5/35; A61B 7/04; A61B 7/00; G16H 40/63
  See application file for complete search history.

(56) References Cited

U.S. PATENT DOCUMENTS

| | | |
|---|---|---|
| 6,442,408 B1 | 8/2002 | Wenzel et al. |
| 6,456,870 B1 | 9/2002 | Rennert et al. |
| 6,475,800 B1 | 11/2002 | Hazen et al. |
| 6,493,566 B1 | 12/2002 | Ruchti et al. |
| 6,501,982 B1 | 12/2002 | Ruchti et al. |
| 6,512,936 B1 | 1/2003 | Monfre et al. |
| 6,512,937 B2 | 1/2003 | Blank et al. |
| 6,587,702 B1 | 7/2003 | Ruchti et al. |
| 6,668,181 B2 | 12/2003 | Wenzel et al. |
| 6,671,542 B2 | 12/2003 | Rennert et al. |
| 6,675,029 B2 | 1/2004 | Monfre et al. |
| 6,697,654 B2 | 2/2004 | Lorenz et al. |
| 6,777,240 B2 | 8/2004 | Hazen et al. |
| 6,864,978 B1 | 3/2005 | Hazen et al. |
| 7,006,856 B2 | 2/2006 | Baker, Jr. et al. |
| 7,038,774 B2 | 5/2006 | Hazen et al. |
| 7,436,511 B2 | 10/2008 | Ruchti et al. |
| RE41,333 E | 5/2010 | Blank et al. |
| 8,095,192 B2 | 1/2012 | Baker, Jr. et al. |
| 8,160,686 B2 | 4/2012 | Allavatam et al. |
| 8,160,687 B2 | 4/2012 | Warren et al. |
| 8,265,749 B2 | 9/2012 | Allavatam et al. |
| 8,565,878 B2 | 10/2013 | Allavatam et al. |
| 8,588,896 B2 | 11/2013 | Allavatam et al. |
| 8,600,489 B2 | 12/2013 | Warren et al. |
| 8,626,280 B2 | 1/2014 | Allavatam et al. |
| 8,880,161 B2 | 11/2014 | Warren et al. |
| 8,929,977 B2 | 1/2015 | Allavatam et al. |
| 9,162,074 B2 | 10/2015 | Allavatam et al. |
| 9,265,432 B2 | 2/2016 | Warren et al. |
| 9,339,662 B2 | 5/2016 | Allavatam et al. |
| 9,594,892 B2 | 3/2017 | Bae et al. |
| 9,763,619 B2 | 9/2017 | Warren et al. |
| 9,802,056 B2 | 10/2017 | Allavatam et al. |
| 9,876,791 B2 | 1/2018 | Bae et al. |
| 9,878,172 B2 | 1/2018 | Allavatam et al. |
| 9,962,126 B2 | 5/2018 | Maeda et al. |
| 10,220,219 B2 | 3/2019 | Allavatam et al. |
| 10,709,379 B2 | 7/2020 | Warren et al. |
| 10,898,080 B2 | 1/2021 | Feng et al. |
| 10,974,058 B2 | 4/2021 | Allavatam et al. |
| 2002/0137995 A1* | 9/2002 | Heckel ................. A61B 5/6843 600/323 |
| 2004/0138540 A1 | 7/2004 | Baker, Jr. et al. |
| 2005/0197549 A1* | 9/2005 | Baker, Jr. ............ A61B 5/7203 600/323 |
| 2006/0106571 A1 | 5/2006 | Kim et al. |
| 2006/0135860 A1 | 6/2006 | Baker, Jr. et al. |
| 2006/0167350 A1 | 7/2006 | Monfre et al. |
| 2007/0239220 A1* | 10/2007 | Greenhut ............. A61B 5/7221 607/32 |
| 2009/0192394 A1* | 7/2009 | Guttag ................. A61B 5/7275 600/509 |
| 2010/0090798 A1 | 4/2010 | Garcia Molina et al. |
| 2010/0280402 A1 | 11/2010 | Dunbar et al. |
| 2012/0016249 A1* | 1/2012 | Lian ...................... A61B 5/349 600/509 |
| 2012/0302900 A1 | 11/2012 | Yin et al. |
| 2013/0079601 A1* | 3/2013 | Addison .............. A61B 5/7221 600/300 |
| 2013/0131539 A1 | 5/2013 | Aberg et al. |
| 2014/0180044 A1 | 6/2014 | Addison et al. |
| 2014/0275872 A1 | 9/2014 | Merritt et al. |
| 2016/0191517 A1 | 6/2016 | Bae et al. |
| 2016/0228022 A1 | 8/2016 | Hayashi et al. |
| 2016/0287110 A1 | 10/2016 | Morris et al. |
| 2017/0027525 A1 | 2/2017 | Park et al. |
| 2017/0055920 A1 | 3/2017 | Mestha et al. |
| 2017/0128019 A1 | 5/2017 | Shao et al. |
| 2018/0021590 A1 | 1/2018 | Allavatam et al. |
| 2018/0122066 A1 | 5/2018 | Prasad et al. |
| 2019/0029600 A1 | 1/2019 | Hutchinson |
| 2021/0153756 A1 | 5/2021 | Hubner |
| 2021/0205558 A1 | 7/2021 | Vicario et al. |

FOREIGN PATENT DOCUMENTS

| | | |
|---|---|---|
| JP | 2003-534530 A | 11/2003 |
| JP | 2006-512973 A | 4/2006 |
| JP | 2010-504793 A | 2/2010 |
| JP | 2012-502670 A | 2/2012 |
| JP | 2014-176584 A | 9/2014 |
| JP | 2016-45939 A | 4/2016 |
| KR | 10-1270954 B1 | 6/2013 |
| KR | 10-2013-0098141 A | 9/2013 |
| KR | 10-2016-0082081 A | 7/2016 |
| KR | 10-2017-0012924 A | 2/2017 |
| WO | 2004062492 A1 | 7/2004 |
| WO | 2011134489 A1 | 11/2011 |
| WO | 2017093150 A1 | 6/2017 |
| WO | 2018137300 A1 | 8/2018 |

OTHER PUBLICATIONS

Chou, "The Research on Dynamic Pulse Signal Detection and Real-time Pulse Rate Variability Extraction and Analysis," Doctoral Electronic Journal, Dec. 2015, Total 169 pages.
Li et al., "Signal Quality Estimation of 12-lead Electrocardiogram by Waveform Morphology," Space Medicine and Medical Engineering, vol. 28, No. 6, pp. 419-426, Dec. 2015.
Communication dated Apr. 9, 2019, issued by the European Patent Office in counterpart European Application No. 18209231.2.
W Karlen et al. "Photoplethysmogram signal quality estimation using repeated Gaussian filters and cross-correlation," Sep. 2012, Physiol. Meas. vol. 33, 2012, (pp. 1617-1629).
Communication dated Jul. 15, 2020, issued by the European Patent Office in counterpart European Application No. 18209231.2.
Communication dated Mar. 8, 2022 issued by the Japanese Intellectual Property Office in counterpart Japanese Application No. 2018-224468.
Krishnan et al., "Two-Stage Approach for Detection and Reduction of Motion Artifacts in Photoplethysmographic Data", Aug. 2010, IEEE Transactions on Biomedical Engineering, vol. 57, No. 8, pp. 1867-1876 (11 pages total).
Selvaraj et al., "Statistical Approach for the Detection of Motion/Noise Artifacts in Photoplethysmogram", Aug. 2011, 33rd Annual International Conference of the IEEE EMBS, pp. 4972-4975 (5 pages total).
Elgendi, M. "Optimal Signal Quality Index for Photoplethysmogram Signals", Sep. 22, 2016, Bioengineering 2016, 3, 21, pp. 1-15 (15 pages total).

* cited by examiner

BIO-SIGNAL QUALITY ASSESSMENT APPARATUS AND BIO-SIGNAL QUALITY ASSESSMENT METHOD

CROSS-REFERENCE TO RELATED APPLICATION

This is a Continuation application of U.S. application Ser. No. 16/200,141 filed Nov. 26, 2018, which claims priority from Korean Patent Application No. 10-2017-0164562, filed on Dec. 1, 2017 in the Korean Intellectual Property Office and Korean Patent Application No. 10-2018-0076515, filed on Jul. 2, 2018 in the Korean Intellectual Property Office, the disclosures of which are incorporated herein in their entireties.

BACKGROUND

1. Field

Apparatuses and methods consistent with exemplary embodiments relate to assessing the quality of a bio-signal obtained from an object.

2. Description of the Related Art

When bio-information is measured or estimated from a bio-signal, the quality of a measured bio-signal affects reliability of the measured or estimated bio-information.

As a method of assessing the quality of a bio-signal, there is a method of assessing quality of a bio-signal based on a signal-to-noise ratio (SNR) by calculating a spectrum of the frequency of the bio-signal, calculating power in a frequency range of the bio-signal, in which valid bio information is included, and calculating power in other frequency ranges of the bio-signal.

Further, there is also a method of assessing the quality of a bio-signal, in which the number of alternating positive and negative values of a bio-signal is calculated based on the value of 0, and if there is a larger number of zero-crossing points, it is assessed that the quality of the bio-signal is low.

Recently, there has been research to develop a method of assessing the quality of a bio-signal by using a smaller device and a limited amount of computation of a processor with high sensitivity and specificity for distinguishing between a signal and noise.

SUMMARY

Exemplary embodiments address at least the above problems and/or disadvantages and other disadvantages not described above. Also, the exemplary embodiments are not required to overcome the disadvantages described above, and may not overcome any of the problems described above.

According to an aspect of an exemplary embodiment, there is provided a bio-signal quality assessment apparatus including: a bio-signal obtainer configured to obtain a bio-signal; and a processor configured to extract periodic signals from the obtained bio-signal, and determine a signal quality index based on at least one of similarity between the extracted periodic signals and signal variability of the obtained bio-signal.

In response to at least one of the extracted periodic signals having a different duration from other periodic signals, the processor may perform preprocessing on the at least one extracted periodic signal to calculate the similarity between the extracted periodic signals.

In this case, the processor may perform resampling on the extracted periodic signals so that each of the extracted periodic signals may have an equal number of samples N.

Further, the processor may determine a similarity evaluation period in each of the extracted periodic signals, and may calculate the similarity between the extracted periodic signals in the determined similarity evaluation period.

In addition, the processor may calculate the similarity between the extracted periodic signals which are apart from each other by a predetermined distance.

The processor may calculate the similarity between the extracted periodic signals and a reference signal, and determine, as the reference signal, an average signal of the extracted periodic signals which is obtained by superimposing the extracted periodic signals.

The processor may determine the signal quality index based on statistical information of the calculated similarity between the periodic signals.

In this case, the processor may determine the signal quality index based on a combination of two or more K-adjacent similarities having different K values. The K values may indicate distance between the extracted periodic signals.

Further, the processor may determine a signal analysis period so that at least one of the periodic signals is to be included.

Moreover, the processor may calculate the signal variability, including at least one of amplitude variability and time variability of the obtained bio-signal, and may determine the signal quality index based on the calculated signal variability.

Further, the processor may calculate a standard deviation or a coefficient of variation of at least one of amplitudes and durations of the extracted periodic signals, and may calculate the signal quality index based on the calculated standard deviation or the calculated coefficient of variation.

The bio-signal quality assessment apparatus may further include an output interface configured to output at least one of the obtained bio-signal, the extracted periodic signals, a similarity evaluation period, a signal analysis period, a reference signal, the similarity between the periodic signals, the signal variability, and the signal quality index.

Further, the bio-signal may include at least one of electrocardiogram (ECG), photoplethysmography (PPG), ballistocardiogram (BCG), a heart sound.

According to an aspect of another exemplary embodiment, there is provided a bio-signal quality assessment method including: obtaining a bio-signal; and extracting periodic signals from the obtained bio-signal; and determining a signal quality index based on at least one of similarity between the extracted periodic signals and signal variability of the obtained bio-signal.

Further, the bio-signal quality assessment method may further include, in response to at least one of the extracted periodic signals having a different duration from other periodic signals, preprocessing the at least one extracted periodic signal to calculate the similarity between the extracted periodic signals.

In this case, the preprocessing may include resampling the extracted periodic signals so that each of the extracted periodic signals may have an equal number of samples N.

In addition, the preprocessing may include determining a similarity evaluation period in each of the extracted periodic signals, and calculating the similarity between the extracted periodic signals in the determined similarity evaluation period.

The determining the signal quality index may further include calculating similarity between the extracted periodic signals which are apart from each other by a predetermined distance.

Moreover, the determining the signal quality index may further include calculating the similarity between the extracted periodic signals and a reference signal, and the calculating the similarity may further include determining, as the reference signal, an average signal of the extracted periodic signals which is obtained by superimposing the extracted periodic signals.

Further, the determining the signal quality index may include determining the signal quality index based on at least one of a combination of two or more K-adjacent similarities having different K values, and statistical information of the calculated similarity between the extracted periodic signals. The K values may indicate distance between the extracted periodic signals.

In addition, the determining the signal quality index may include determining the signal quality index by calculating signal variability, including at least one of amplitude variability and time variability of the obtained bio-signal, and determining the signal quality index based on the calculated signal variability.

Further, the determining the signal quality index may include determining a standard deviation or a coefficient of variation of at least one of amplitudes and durations of the extracted periodic signals, and determining the signal quality index based on the determined standard deviation or the determined coefficient of variation.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
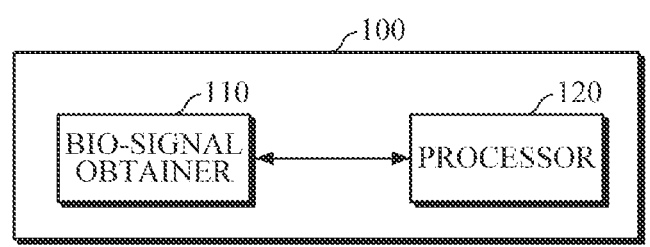
FIG. 1 is a block diagram illustrating a bio-signal quality assessment apparatus according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

Process steps described herein may be performed differently from a specified order, unless a specified order is clearly stated in the context of the disclosure. That is, each step may be performed in a specified order, at substantially the same time, or in a reverse order.

Further, the terms used throughout this specification are defined in consideration of the functions according to exemplary embodiments, and can be varied according to a purpose of a user or manager, or precedent and so on. Therefore, definitions of the terms should be made on the basis of the overall context.

Any references to singular may include plural unless expressly stated otherwise. In the present specification, it should be understood that the terms, such as 'including' or 'having,' etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Expressions such as "at least one of," when preceding a list of elements, modify the entire list of elements and do not modify the individual elements of the list.

FIG. 1 is a block diagram illustrating a bio-signal quality assessment apparatus according to an exemplary embodiment. The bio-signal quality assessment apparatus 100 may extract one or more periodic signals from an obtained bio-signal, and may determine a signal quality index based on at least one of similarity between the extracted periodic signals and signal variability of the obtained bio-signal.

The bio-signal quality assessment apparatus 100 may determine a signal analysis period in the obtained bio-signal for calculating a signal quality index, and may extract one or more periodic signals for determining similarity in the signal analysis period.

The bio-signal quality assessment apparatus 100 may assess the quality of a bio-signal by calculating similarity between the extracted periodic signals.

Since the bio-signal is not suddenly changed during a short period of time to maintain homeostasis, the bio-signal quality assessment apparatus 100 may assess the quality of a bio-signal based on similarity between waveforms of the extracted periodic signals.

For example, the bio-signal quality assessment apparatus 100 may perform preprocessing by resampling the extracted periodic signals or extracting some portion of the periodic signal as a similarity evaluation period, and may assess the quality of the bio-signal by calculating similarity between the preprocessed periodic signals.

In another example, the bio-signal quality assessment apparatus 100 may assess the quality of the obtained bio-signal based on a signal variability in the signal analysis period. For example, the bio-signal quality assessment apparatus 100 may calculate a signal variability of the obtained bio-signal based on an amplitude change of a bio-signal in the signal analysis period or a duration of each of the extracted periodic signals, and may assess the quality of the bio-signal based on the calculated variability of the bio-signal.

In this case, the bio-signal quality assessment apparatus 100 may first calculate the signal variability of the obtained bio-signal and then calculate similarity between periodic signals for bio-signals having low variability; or the bio-signal quality assessment apparatus 100 may first calculate the similarity between periodic signals and then calculate the variability of the bio-signal, thereby imparting reliability to the calculated similarity between periodic signals.

However, the calculation is not limited thereto, and the similarity between periodic signals and the variability of the bio-signal may be calculated selectively, in parallel, and/or sequentially.

The bio-signal quality assessment apparatus 100 may be implemented as a software module or manufactured in the form of a hardware chip to be embedded in various types of electronic devices. In this case, examples of the electronic devices may include a cellular phone, a smartphone, a tablet PC, a laptop computer, a personal digital assistant (PDA), a portable multimedia player (PMP), a navigation, an MP3 player, a digital camera, and a wearable device. However, the electronic device is not limited to the above examples, and may include various devices.

Hereinafter, the quality assessment of a bio-signal, which is performed by the bio-signal quality assessment apparatus, will be described in detail with reference to FIGS. 1 to 5B.

Referring to FIG. 1, the bio-signal quality assessment apparatus 100 includes a bio-signal obtainer 110 and a processor 120. Here, the processor 120 may be one or more processors or memories, or a processing module including a combination thereof.

The bio-signal obtainer 110 may obtain a bio-signal of a user.

Here, the bio-signal may include electrocardiogram (ECG), photoplethysmography (PPG), ballistocardiogram (BCG), a heart sound, impedance cardiograph (ICG), impedance plethysmograph (IPG), a pressure wave at the radial artery, a periodic signal occurring by repetitive movement of a human body (e.g., walking, blinking, etc.), and a change in an in vivo component.

For example, the bio-signal obtainer 110 may further include a sensor which includes at least one of the following: one or more electrodes for measuring a bio-signal, a pressure sensor, a spectrometer, a body impedance measuring circuit, and a light detection module having a light source and a light detector. The bio-signal obtainer 110 may obtain a bio-signal by directly interfacing with a user through the sensor.

Further, the bio-signal obtainer 110 may communicate with an external device to receive bio-signal data of a user from the external device. For example, the bio-signal obtainer 110 may receive bio-signal data of a user from the external device by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, and the like. Examples of the external device may include a cellular phone, a smartphone, a tablet PC, a laptop computer, a personal digital assistant (PDA), a portable multimedia player (PMP), a navigation, an MP3 player, a digital camera, and a wearable device. However, the external device is not limited to the above examples, and may be various devices for storing bio-signal data of a user.

The processor 120 may extract one or more periodic signals from the obtained bio-signal, and may calculate a signal quality index based on at least one of similarity between the extracted periodic signals and variability of the bio-signal.

For example, the processor 120 may determine a signal analysis period in the obtained bio-signal to calculate a signal quality index.

Figure 2:
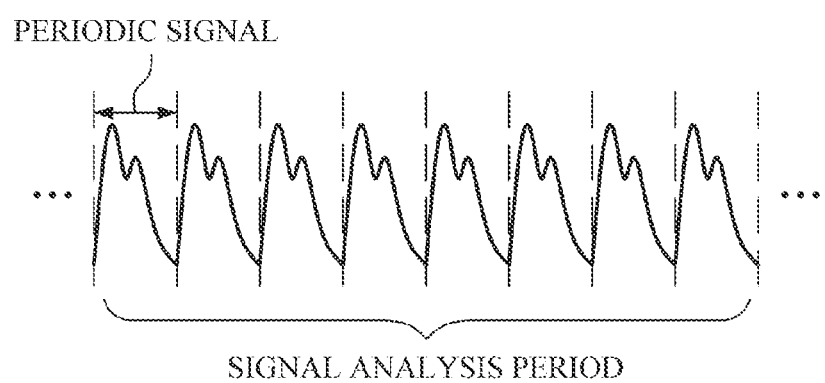
FIG. 2 is a diagram illustrating segmentation of a bio-signal according to an exemplary embodiment.

FIG. 2 is a diagram illustrating segmentation of a bio-signal according to an exemplary embodiment.

Referring to FIGS. 1 and 2, the processor 120 may determine a signal analysis period, in which one or more periodic signals are included, in the obtained bio-signal.

For example, when quality of a PPG signal is assessed, the processor 120 may determine a signal analysis period of the PPG signal based on a frequency of the PPG signal, which is generally within a range of about 0.4 Hz to 10 Hz. The processor 120 may determine any 15-second period in the PPG signal as the signal analysis period, so that PPG waveforms may be detected from the PPG signal about 15 times.

However, the determination is not limited thereto, and according to a computation capability and/or a user's setting, the processor 120 may determine a bio-signal during a predetermined time (e.g., about 10 seconds) to be a signal analysis period for calculating a signal quality index.

Further, the processor 120 may determine a plurality of signal analysis periods in the bio-signal.

The processor 120 may extract one or more periodic signals from the obtained bio-signal.

Referring back to FIGS. 1 and 2, in the case where the obtained bio-signal is a bio-signal having periodicity, the processor 120 may extract periodic signals from the obtained bio-signal by segmenting the bio-signal in units of one period. For example, the processor 120 may extract the periodic signals by detecting feature points (e.g., PPG onset, maximum slope point, maximum point of second derivative of PPG, intersecting tangent point, etc.) from the obtained bio-signal.

Further, the processor 120 may perform preprocessing to calculate similarity based on the one or more extracted periodic signals. For example, in the case where the periodic signals are extracted based on feature points of the bio-signal rather than in equal time unit, the length, duration, or duration time of each of the extracted periodic signals may be different.

For example, if at least one of the extracted periodic signals has a different duration from other periodic signals, the processor 120 may perform preprocessing of the extracted periodic signal to calculate similarity between the extracted periodic signals.

Figure 3A:
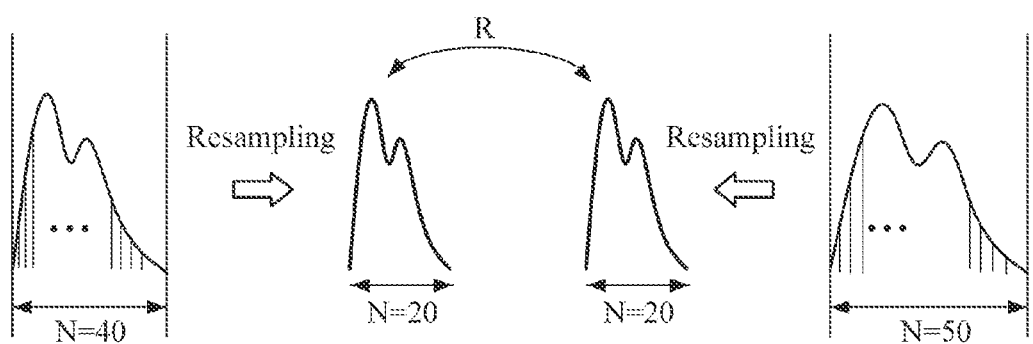
FIG. 3A is a diagram illustrating preprocess of a bio-signal according to an exemplary embodiment.

FIG. 3A is a diagram illustrating preprocess of a bio-signal according to an exemplary embodiment.

Referring to FIGS. 1 and 3A, the processor 120 may perform resampling of at least one of the extracted periodic signals so that the extracted periodic signals have an equal number of samples N. For example, the bio-signal obtained by the bio-signal obtainer 110 may be sampled at an equal sampling rate and may be measured and/or received. In this case, if at least one of the extracted periodic signals has a different length and/or duration from other periodic signals, the number of samples N of the extracted periodic signals may be different from each other, such that it may not be appropriate to calculate similarity of waveforms between the periodic signals by comparing periodic signals having different lengths and/or durations.

Accordingly, in the case where at least one of the extracted periodic signals has a different length and/or duration from other periodic signals, the processor 120 may perform preprocessing by resampling the extracted periodic signal so that each of the extracted periodic signals has a predetermined number of samples N. To this end, the processor 120 may perform resampling of each of the extracted periodic signals by adjusting a sampling rate.

For example, in the case where a first periodic signal and a second periodic signal have different lengths and/or durations from each other, and the processor 120 performs sampling of the two signals at the same sampling rate (e.g., 40 Hz), the number of samples N of the first periodic signal and the second periodic signal may be different from each other (e.g., 40 samples and 50 samples are obtained from the first periodic signal and the second period signal, respectively if the first extracted periodic signal and the second extracted periodic signal have different durations of 1 second and 1.25 seconds, respectively, but the same rate of 40 Hz is applied to both of the first extracted periodic signal and the second extracted periodic signal). In this case, the processor 120 may perform resampling of the first periodic signal at a sampling rate of 20 Hz, and may perform resampling of the second periodic signal at a sampling rate of 16 Hz, so that the first periodic signal and the second periodic signal may have an equal number of samples N (e.g., N=20 samples).

In this manner, as the processor 120 may perform resampling of each of the extracted periodic signals at different sampling rates, the processor 120 may calculate similarity R between periodic signals having different durations from each other.

However, this is merely an example of the processor 120, and even when at least one of the extracted periodic signals has a different length and/or duration from other periodic signals, the processor 120 may calculate similarity between periodic signals at the same sample point by resampling the periodic signals while varying a sampling rate of each of the periodic signals if necessary.

Figure 3B:
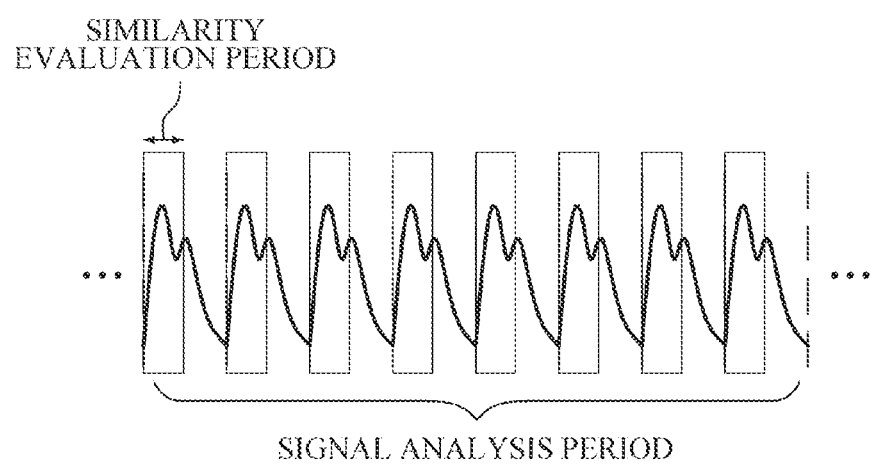
FIG. 3B is a diagram illustrating preprocess a bio-signal according to another exemplary embodiment.

FIG. 3B is a diagram illustrating preprocess of a bio-signal according to another exemplary embodiment.

For example, the processor 120 may determine a similarity evaluation period in each of the extracted periodic signals, and may calculate similarity between the periodic signals in the determined similarity evaluation period.

Referring to FIGS. 1 and 3B, in the case where at least one of the extracted periodic signals has a different length and/or duration from other periodic signals, the processor 120 may extract some portion (e.g., initial 30 samples of each periodic signal, etc.) of each periodic signal, and may determine the extracted portion as the similarity evaluation period.

However, the determination is not limited thereto, and based on a computation amount of the processor 120 and a power supply state of a bio-signal quality assessment apparatus (residual quantity of a battery when being embedded in a mobile terminal), the processor 120 may perform preprocessing by determining some portion of the extracted periodic signals to be a similarity evaluation period, and may calculate similarity between the periodic signals only in the similarity evaluation period, instead of calculating similarity for the entire portions of each of the periodic signals. In this manner, the processor 120 may perform rapid calculation by using a limited computation capability.

In this case, the similarity may be calculated by using a similarity evaluation index including a correlation coefficient, dynamic time warping (DTW), and signal difference of periodic signals. However, the similarity evaluation index is merely exemplary, and the processor 120 may use various similarity evaluation indices indicative of similarity between periodic signals.

For convenience of explanation, the above explanation is described based on an example where the processor 120 performs preprocessing of the extracted periodic signals in the case where at least one of the extracted periodic signals has a different duration from other periodic signals. However, the operation of the processor 120 is not limited thereto, and may perform preprocessing of the extracted periodic signals to calculate similarity between the extracted periodic signals.

The processor 120 may calculate similarity between the extracted periodic signals and at least one of a K-adjacent periodic signal and a reference signal for each of the periodic signals.

For example, the processor 120 may calculate similarity between each of the extracted periodic signals and a periodic signal which is K-adjacent to each of the extracted periodic signals.

Figure 4:
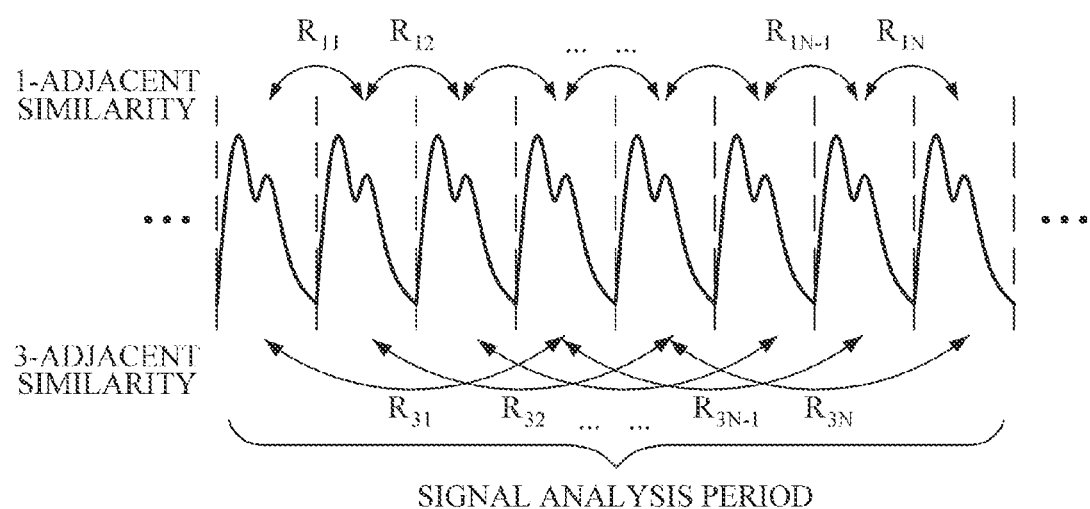
FIG. 4 is a diagram illustrating calculation of K-adjacent similarity of a periodic signal according to an exemplary embodiment.

FIG. 4 is a diagram illustrating calculation of K-adjacent similarity of periodic signals according to an exemplary embodiment.

The K-adjacent periodic signal may indicate a periodic signal (L+K-th periodic signal) which is spaced apart by K from any one periodic signal (e.g., L-th periodic signal) of the extracted periodic signals, in which K may be an integer number.

For example, referring to FIGS. 1 and 4, the processor 120 may calculate similarity between each of the extracted periodic signals and a periodic signal which is spaced apart by K from each of the extracted periodic signals. In this case, the processor 120 may calculate similarity between the extracted periodic signals by calculating similarities between all the extracted periodic signals and periodic signals which are spaced apart therefrom by K. If K is 1, the processor 120 may calculate similarities R11, R12, . . . , and R1*n* between all the adjacent periodic signals and each of the extracted periodic signals.

In another example, the processor 120 may calculate similarity between the extracted periodic signals and the reference signal.

Here, the reference signal may be any one periodic signal among the extracted periodic signals, or may be an average signal (e.g., ensemble average) of the extracted periodic signals, which is obtained by superimposing the extracted periodic signals.

For example, the processor 120 may determine, as the reference signal, an average signal (e.g., ensemble average) of the extracted periodic signals, which is obtained by superimposing the extracted periodic signals, and may calculate similarity between the average signal and the extracted periodic signals. Further, the processor 120 may determine, as the reference signal, a periodic signal which is extracted first among the extracted periodic signals; or may select any one periodic signal, having an average amplitude or duration value, from among the extracted periodic signals, and may determine the periodic signal to be the reference signal.

The processor 120 may calculate similarities R1, R2, . . . , and Rn by comparing the reference signal with each of the extracted periodic signals.

The processor 120 may calculate a signal quality index based on statistical information of the calculated similarities between the periodic signals and/or a combination of the similarities. In this case, the statistical information may be, but is not limited to, an average, a standard deviation, dispersion, a coefficient of variation, and a coefficient of quartile deviation.

For example, in the case of calculating the similarities R1, R2, . . . , and Rn by comparing the reference signal with each of the periodic signals, the processor 120 may calculate an average value ((R1+R2+ . . . +Rn)/n) of the calculated similarities, and may determine a signal quality index (SQI) based on the average value of the calculated similarities.

The processor 120 may calculate the signal quality index (SQI) based on a combination of two or more K-adjacent similarities having different K values. For example, FIG. 4 illustrates an example of calculating similarities between periodic signals in the case where K values are 4 and 3.

For example, the processor 120 may multiply (e.g., multiply an average value of 1-adjacent similarities and an average value of M/2-adjacent similarities, where M is the number of extracted periodic signals), add, or divide average values of two or more K-adjacent similarities having different K values, or may apply the average values to a function, and may determine a value obtained as a result of the calculation to be the signal quality index (SQI).

In the case where K values are I and J (I≠J), the processor 120 may calculate the signal quality index (SQI) by respectively calculating I-adjacent similarities RI1, RI2, . . . , and Rin, and J-adjacent similarities RJ1, RJ2, . . . , and RJn, and by combining statistics (e.g., average) of the I-adjacent similarities and the J-adjacent similarities. For example, the processor 120 may calculate, as the signal quality index (SQI), a value obtained by multiplying the I-adjacent similarities RI1, RI2, . . . , and Rin and the J-adjacent similarities RJ1, RJ2, . . . , and RJn. In this manner, by combining K-adjacent similarities having different K values, the processor 120 may assess the quality of a bio-signal more clearly.

For example, by comparing a case where an average of the I-adjacent similarities is 0.9 and an average of the J-adjacent similarities is 0.8 with a case (e.g., combined similarity of 0.72) where an average of the I-adjacent similarities is multiplied with an average of the J-adjacent similarities, the processor 120 may more clearly determine whether the periodic signals of the obtained bio-signal have a similar waveform in the signal analysis period.

Further, based on the calculated similarities R1, R2, . . . , and Rn, the processor 120 may selectively remove a periodic signal, which occurs irregularly such as motion noise or arrhythmia, from the extracted periodic signals.

For example, in the case of calculating similarity between a first extracted periodic signal and a second extracted periodic signal which is spaced apart by K from the first extracted periodic signal, the processor 120 may select the first and second extracted periodic signals if a similarity value of the first and second extracted periodic signals is equal to or lower than a predetermined threshold value (e.g., R=0.6) from among the calculated similarities R1, R2, . . . , and Rn. The processor 120 may determine a periodic signal, which occurs irregularly, based on a relationship between the first and second extracted periodic signals and other periodic signals. The processor 120 may calculate the similarity after removing the irregularly occurring periodic signal.

In another example, in the case of determining an average signal of the extracted periodic signals, which is obtained by superimposing the extracted periodic signals, to be the reference signal, and calculating similarity between the reference signal and the extracted periodic signals, the processor 120 may select a periodic signal having a similarity value equal to or lower than a predetermined threshold value (e.g., R=0.6) from among the calculated similarities R1, R2, . . . , and Rn, and may calculate the similarity after removing the selected periodic signal.

As described above, by calculating similarity by removing only an irregular signal, caused by arrhythmia or motion noise, from the obtained bio-signal, there is no need to re-obtain a bio-signal unnecessarily, such that the processor 120 may obtain a prompt result in response to a user's request for bio-signal quality assessment, and reliability of the quality assessment of the obtained bio-signal may be guaranteed.

However, this is merely an example of the processor 120, and instead of removing only the periodic signal occurring irregularly from the obtained bio-signal, the processor 120 may control the bio-signal obtainer 110 to re-obtain a bio-signal, and may re-determine a signal analysis period in the obtained bio-signal.

The processor 120 may calculate a signal variability of the obtained bio-signal. The signal variability may be a value obtained by tracking a variability rate of features values of the obtained bio-signal.

Figure 5A:
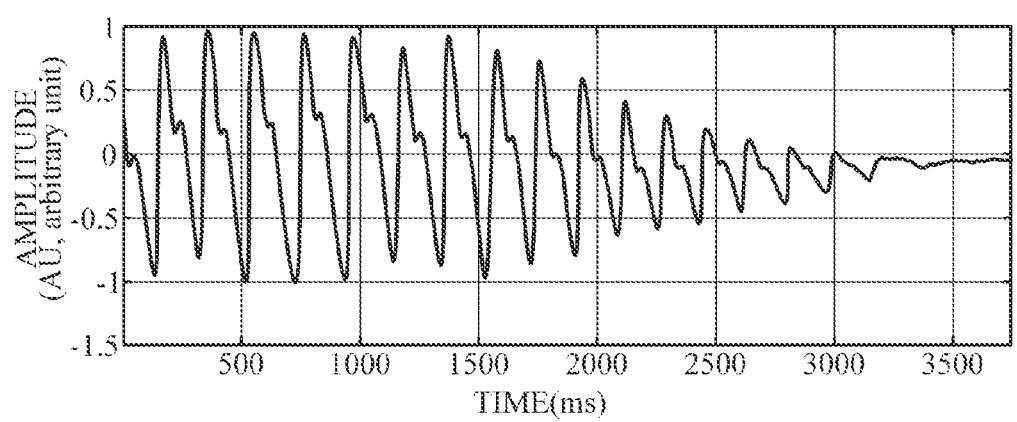
FIG. 5A is a diagram illustrating amplitude variability of a bio-signal according to an exemplary embodiment.
Figure 5B:
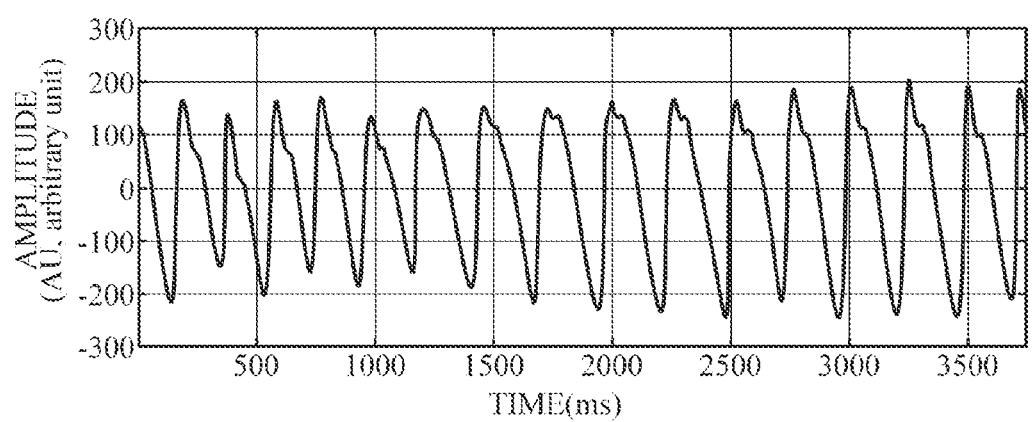
FIG. 5B is a diagram illustrating time variability of a bio-signal according to an exemplary embodiment.

FIG. 5A is a diagram illustrating amplitude variability of a bio-signal according to an exemplary embodiment. FIG. 5B is a diagram illustrating time variability of a bio-signal according to an exemplary embodiment.

The processor 120 may calculate signal variability including at least one of the amplitude variability and the time variability of the obtained bio-signal, and may calculate a signal quality index based on the calculated signal variability.

For example, the processor 120 may calculate an average of amplitudes of the extracted periodic signals. When a difference between an amplitude of each of extracted periodic signals and the calculated average of amplitudes exceeds a predetermined reference value, the processor 120 may determine the quality of the obtained bio-signal to be low. For example, in the case where a difference between the amplitude of each of extracted periodic signals and the calculated average of amplitudes exceeds 20%, the processor 120 may determine a quality index of the obtained bio-signal to be 0.

In another example, the processor 120 may calculate a standard deviation or a coefficient of variation of amplitudes of the extracted periodic signals and may calculate a signal quality index based on the calculated standard deviation or the calculated coefficient of variation of the amplitudes of the extracted periodic signals. The signal quality index may be inversely proportional to the standard deviation or the coefficient of variation of the amplitudes of the extracted periodic signals.

In another example, the processor 120 may calculate an average duration of each of the periodic signals extracted from the obtained bio-signal, and if a difference between a duration of each of the extracted periodic signals and the calculated average duration exceeds a predetermined reference value, the processor 120 may determine the quality of the obtained bio-signal to be low. For example, in the case where a difference between the duration of each of the extracted periodic signals and the calculated average duration exceeds 20%, the processor 120 may determine a quality index of the obtained bio-signal to be 0.

In another example, the processor 120 may calculate a standard deviation or a coefficient of variation of durations of the extracted periodic signals and may calculate a signal quality index based on the calculated standard deviation or the calculated coefficient of variation of the durations of the extracted periodic signals. The signal quality index may be inversely proportional to the standard deviation or the coefficient of variation of the durations of the extracted periodic signals.

Further, the processor 120 may calculate signal variability of signals of the obtained bio-signal in the signal analysis period determined for calculating a signal quality index. In this case, the processor 120 may calculate the quality of signals in the determined signal analysis period based on the calculated signal variability.

The processor 120 may determine the quality of the obtained bio-signal based on the signal quality index.

For example, the processor 120 may calculate a signal quality index according to the types of similarity evaluation index, and may determine the quality of the obtained bio-signal based on the calculated signal quality index. In the case where the similarity evaluation index is a correlation coefficient, a result may be obtained indicating that when R=1, similarity between the periodic signals of the obtained bio-signal may be the highest. In this case, the signal quality index may be determined to be 1, and the processor 120 may assess that the quality of the obtained bio-signal is high based on the result. The similarity evaluation index has a value in the range from 0 to 1, where the value of 1 indicates the highest correlation, and the value of 0 indicates the lowest correlation.

In addition, in the case where the similarity evaluation index is a signal difference, a result may be obtained indicating that when a calculated signal difference has a smaller value, similarity between the periodic signals of the obtained bio-signal may be the highest. In this case, the processor 120 may calculate a signal quality index based on the signal difference value, and may assess the quality of the obtained bio-signal based on the calculated signal quality index.

Further, the processor 120 may calculate reliability of bio-information based on the calculated signal quality index. Here, when the bio-information is estimated based on the obtained bio-signal, the bio-information reliability may indicate a degree of reliability of accuracy of the estimated bio-information.

For example, in the case where the similarity evaluation index is a correlation coefficient, and the calculated signal quality index is 0.8, when estimating bio-information based on the obtained bio-signal, the processor 120 may determine reliability of the estimated bio-information to be about 80%.

In another example, the processor 120 may calculate a signal quality index of the bio-signal according to a degree of signal variability.

For example, the processor 120 may calculate an average of amplitudes of the periodic signals extracted from the obtained bio-signal; and if a difference between an amplitude of each of extracted periodic signals and the calculated average of amplitudes exceeds a predetermined reference value, the processor 120 may calculate a signal quality index according to a degree of excess. In the case where the calculated signal variability exceeds a predetermined threshold value (e.g., an amplitude of any one of the extracted periodic signals exceeds an average of amplitudes of the obtained bio-signal by 20%), the processor 120 may determine the signal quality index to be 0. When the difference between the amplitude of each of the extracted periodic signals and the calculated average of amplitudes is within the predetermined threshold value, the signal quality index may be in inverse proportion to the degree of excess.

In another example, the processor 120 may calculate a standard deviation or a coefficient of variation of amplitudes of the extracted periodic signals and may calculate a signal quality index based on the calculated standard deviation or the calculated coefficient of variation of the amplitudes of the extracted periodic signals. The signal quality index may be inversely proportional to the standard deviation or the coefficient of variation of the amplitudes of the extracted periodic signals.

In another example, the processor 120 may calculate an average duration of each of the periodic signals extracted from the obtained bio-signal; and if a difference between a duration of each of the extracted periodic signals and the calculated average duration exceeds a predetermined reference value (e.g., if a duration of any one of the extracted periodic signals exceeds an average duration of the obtained bio-signal by 20%), the processor 120 may determine the signal quality index to be 0. When the difference between the duration of each of the extracted periodic signals and the calculated average duration is within the predetermined reference value, the signal quality index may be in inverse proportion to the difference.

In another example, the processor 120 may calculate a standard deviation or a coefficient of variation of durations of the extracted periodic signals and may calculate a signal quality index based on the calculated standard deviation or the calculated coefficient of variation of the durations of the extracted periodic signals. The signal quality index may be inversely proportional to the standard deviation or the coefficient of variation of the durations of the extracted periodic signals.

Further, the processor 120 may measure bio-information based on the obtained bio-signal according to the signal quality index of the obtained bio-signal.

For example, in the case where the similarity evaluation index is a correlation coefficient, and the calculated signal quality index is equal to or higher than a predetermined threshold value (e.g., R=0.6), the processor 120 may determine that the obtained bio-signal is 'reliable', and may measure bio-information from the obtained bio-signal. For example, if the obtained bio-signal is a PPG signal, the processor 120 may extract one or more features, having high correlation with bio-information, from the PPG signal, and may measure, as bio-information, blood pressure based on a combination of the extracted features.

The bio-information, which is measured in this manner, is measured based on only the bio-signals, of which reliability is guaranteed by the processor 120, such that reliability of the measured bio-information may be guaranteed.

As described above, the processor 120 may assess the quality of bio-signals which are obtained during a predetermined period of time or continuously, and may measure bio-information from only the bio-signals having reliable quality based on the quality assessment, thereby guaranteeing reliability of the measured bio-information. According to the signal quality index of the obtained bio-signal, the processor 120 may control the bio-signal obtainer 110 to re-obtain a bio-signal.

For example, in the case where the similarity evaluation index is a correlation coefficient, and the calculated signal quality index is lower than a predetermined threshold value (e.g., R=0.6), the processor 120 may determine that the obtained bio-signal is 'unreliable', and may exclude the obtained bio-signal.

In this case, the processor 120 may control the bio-signal obtainer 110 to re-obtain bio-signals of which the number corresponds to the number of excluded bio-signals.

Further, based on a result of quality assessment of the bio-signal, the processor 120 may generate warning information and guide information for accurately obtaining a bio-signal.

For example, among the extracted periodic signals, the processor 120 may specify periodic signals occurring irregularly based on a relationship with other periodic signals. When the periodic signals occurring irregularly exceed a predetermined proportion of the extracted periodic signals (e.g., 25% of the extracted periodic signals), the processor 120 may determine that a bio-signal obtaining state and/or a bio-signal detection state is not good, and may generate warning information.

In another example, upon determining that the bio-signal obtaining state and/or the bio-signal detection state is not good, the processor 120 may generate guide information for accurately obtaining a bio-signal.

For example, in the case where the bio-signal obtainer 110 interfaces with an object to directly obtain a bio-signal by using one or more sensors for measuring a bio-signal, if the bio-signal obtaining state and/or the bio-signal detection state is not good, this may indicate that a contact state of the bio-signal obtainer 110 with the object is poor, the object is moved, or a measurement position of the bio-signal is wrong.

Accordingly, the processor 120 may generate bio-signal measurement guide information to recommend a point to be examined of the object, e.g., a user using the bio-signal quality assessment apparatus 100, to be located at a predetermined measurement position while being in a stable condition, and not to move during a measurement period of time.

In this case, the guide information may include visual information (e.g., images, etc.), acoustic information (e.g., beep sound, etc.), and tactile information (e.g., adjusting intensity of vibration, etc.). For example, the processor 120 may generate guide information, including an image to guide the bio-signal obtainer 110 to be located at a predetermined measurement position, and vibration of which intensity is varied according to whether a point to be examined of the object is properly placed at the predetermined measurement position.

In this manner, by generating guide information to re-measure a bio-signal according to a result of quality assessment of the bio-signal, and by removing a periodic signal having poor quality, the processor 120 may remove an irregular signal occurring by motion noise, and may select only a bio-signal having good quality.

Figure 6:
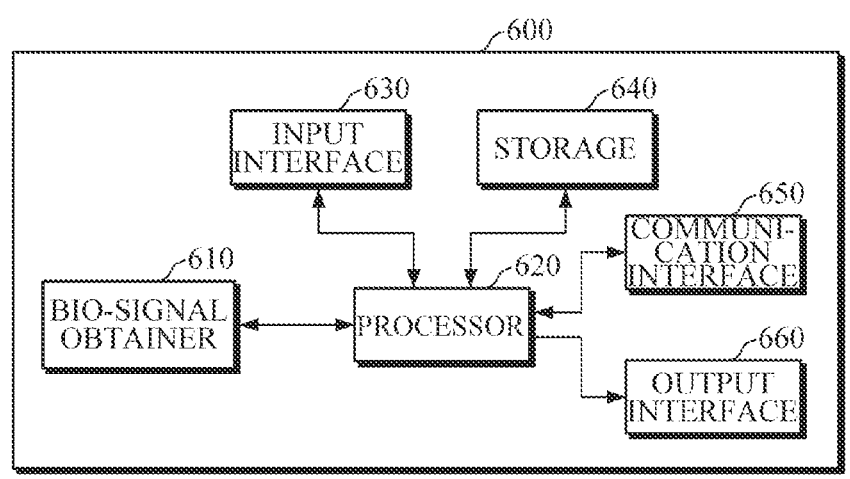
FIG. 6 is a block diagram illustrating a bio-signal quality assessment apparatus according to an exemplary embodiment.

FIG. 6 is a block diagram illustrating a bio-signal quality assessment apparatus according to an exemplary embodiment.

Referring to FIG. 6, the bio-signal quality assessment apparatus includes a bio-signal obtainer 610, a processor 620, an input interface 630, a storage 640, a communication interface 650, and an output interface 660. Here, the bio-signal obtainer 610 and the processor 620 may perform substantially the same function as the bio-signal obtainer 110 and the processor 120 described above with reference to FIG. 1, such that description below will be made based on details that do not overlap.

The input interface 630 may receive input of various operation signals and data required for bio-signal quality assessment from a user.

For example, the input interface 630 may include a keypad, a dome switch, a touch pad (static pressure/capacitance), a jog wheel, a jog switch, and a hardware (H/W) button. Particularly, the touch pad, which forms a layer structure with a display, may be called a touch screen.

For example, the input interface 630 may receive user feature information, which includes one or more of age, gender, stature, weight, body mass index (BMI), and disease history of users, or a measurement position of a bio-signal and types of bio-signal.

The storage 640 may store programs or commands for operation of the bio-signal quality assessment apparatus 600, and may store data input to and output from the bio-signal quality assessment apparatus 600. For example, the storage 640 may store the user feature information input through the input interface 630, the bio-signal data obtained by the bio-signal obtainer 610, similarity, signal variability, and a signal quality index of the bio-signal.

The storage 640 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk. Further, the bio-signal quality assessment apparatus 600 may operate an external storage medium, such as web storage, which performs a storage function of the storage 640 on the Internet.

The communication interface 650 may perform communication with an external device. For example, the communication interface 650 may transmit the user feature information input from a user through the input interface 630, the bio-signal obtained by the bio-signal obtainer 610, a bio-signal quality assessment result of the processor 620 to the external device, or may receive various data, such as the user feature information, the bio-signal, and a reference signal for determining similarity, from the external device.

In this case, the external device may be medical equipment using a bio-signal quality database (DB) and/or a bio-signal quality assessment result, a printer to print out results, or a display to display the bio-signal quality assessment result. In addition, the external device may be a digital TV, a desktop computer, a cellular phone, a smartphone, a tablet PC, a laptop computer, a personal digital assistant (PDA), a portable multimedia player (PMP), a navigation, an MP3 player, a digital camera, and a wearable device, but is not limited thereto.

The communication interface 650 may communicate with an external device by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, third generation (3G) communication, fourth generation (4G) communication, and fifth generation (5G) communication. However, this is merely exemplary and is not intended to be limiting.

The output interface 660 may output at least one of the obtained bio-signal, the extracted periodic signals, the similarity evaluation period, the signal analysis period, the similarity between the periodic signals, the reference signal, the signal variability, and the signal quality index.

For example, the output interface 660 may output at least one of a result of the bio-signal quality assessment, guide and warning information for correcting distortion of the obtained bio-signal, and reliability of the obtained bio-signal by using at least one of an acoustic method, a visual method, and a tactile method. To this end, the output interface 660 may include a display, a speaker, and a vibrator.

For example, upon assessing the quality of a bio-signal, if the processor 620 determines that the obtained bio-signal is distorted or has low reliability, the processor 620 may output an alarm to re-measure a bio-signal through the output interface 660, or may generate guide information for correcting at least one of a contact state of the bio-signal obtainer 610 with an object and a measurement position.

Further, upon determining that it is required to re-measure or re-obtain a bio-signal according to a signal quality index of the obtained bio-signal, the processor 620 may control the bio-signal obtainer 610 to re-obtain a bio-signal. However, the operation of the processor 620 is not limited thereto, and may receive a new bio-signal from an external bio-signal database (DB) through the communication interface 650.

Figure 7:
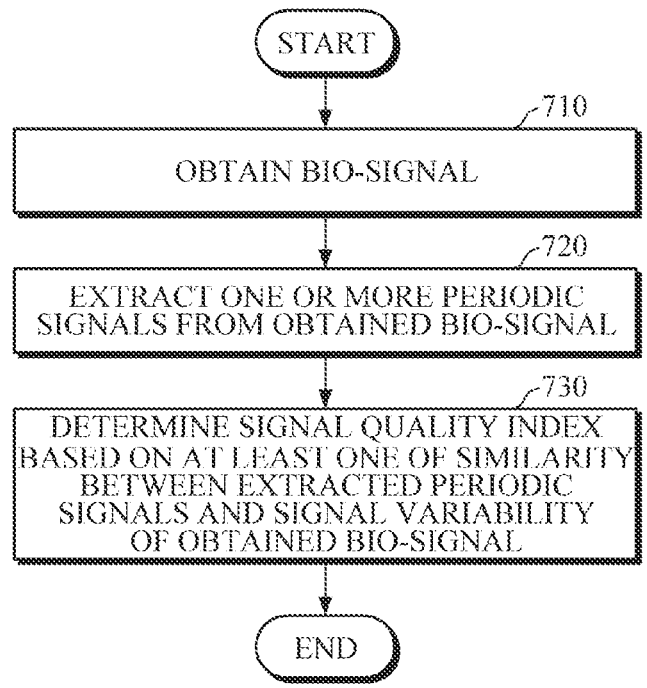
FIG. 7 is a flowchart illustrating a bio-signal quality assessment method according to an exemplary embodiment.

FIG. 7 is a flowchart illustrating a bio-signal quality assessment method according to an exemplary embodiment. The bio-signal quality assessment method of FIG. 7 may be performed by the bio-signal quality assessment apparatus 100 illustrated in FIG. 1.

Referring to FIGS. 1 and 7, the bio-signal quality assessment apparatus 100 may obtain a bio-signal in operation 710.

For example, the bio-signal quality assessment apparatus 100 may include a sensor for measuring a bio-signal, and may obtain a bio-signal by using a sensor which directly interfaces with a user. In another example, the bio-signal quality assessment apparatus 100 may communicate with an external device to receive bio-signal data of a user from the external device.

Upon obtaining the bio-signal, the bio-signal quality assessment apparatus 100 may extract one or more periodic signals from the obtained bio-signal in operation 720.

For example, in the case where the obtained bio-signal is a bio-signal having periodicity, the bio-signal quality assessment apparatus 100 may extract periodic signals from the obtained bio-signal by segmenting the bio-signal in units of one period.

For example, the bio-signal quality assessment apparatus 100 may extract the periodic signals by detecting feature points, such as PPG onset, maximum slope point, maximum point of second derivative of PPG, and intersecting tangent point, from the obtained bio-signal.

Upon extracting the periodic signals from the obtained bio-signal, the bio-signal quality assessment apparatus 100 may determine a signal quality index based on at least one of similarity between the extracted periodic signals and signal variability of the obtained bio-signal in operation 730.

For example, the bio-signal quality assessment apparatus 100 may calculate similarity between the extracted periodic signals and at least one of a K-adjacent periodic signal and a reference signal for each of the periodic signals.

The bio-signal quality assessment apparatus 100 may calculate similarity between each of the extracted periodic signals and a periodic signal which is K-adjacent to each of the extracted periodic signals.

For example, the bio-signal quality assessment apparatus 100 may calculate similarity between each of the extracted periodic signals and a periodic signal which is spaced apart by K from each of the extracted periodic signals. In this case, the bio-signal quality assessment apparatus 100 may calculate similarity between the extracted periodic signals by calculating similarities between all the extracted periodic signals and periodic signals which are spaced apart therefrom by K. If K is 1, the bio-signal quality assessment apparatus 100 may calculate similarities R11, R12, . . . , and R1$n$ between all the adjacent periodic signals and each of the extracted periodic signals.

In addition, the bio-signal quality assessment apparatus 100 may calculate similarity between the extracted periodic signals and the reference signal.

For example, the bio-signal quality assessment apparatus 100 may determine, as the reference signal, an average signal (e.g., ensemble average) of the extracted periodic signals, which is obtained by superimposing the extracted periodic signals, and may calculate similarity between the reference signal and the extracted periodic signals. Further, the bio-signal quality assessment apparatus 100 may determine, as the reference signal, a periodic signal which is extracted first among the extracted periodic signals; or may determine, as the reference signal, any one periodic signal having an average value of amplitudes or durations among the extracted periodic signals The bio-signal quality assessment apparatus 100 may calculate similarities R1, R2, . . . , and Rn by comparing the determined reference signal with each of the extracted periodic signals.

In addition, the bio-signal quality assessment apparatus 100 may determine, as similarity between periodic signals of the obtained bio-signal, statistical information (e.g., an average, a standard deviation, etc.) of a plurality of similarities R1, R2, . . . , and Rn which are calculated by comparing the determined reference signal with each of the periodic signals extracted from the obtained bio-signal.

Further, based on the calculated plurality of similarities R1, R2, . . . , and Rn, the bio-signal quality assessment apparatus 100 may selectively remove a periodic signal, which occurs irregularly such as motion noise, or arrhythmia, from the extracted periodic signals.

For example, in the case of determining, as a reference signal, an average signal of the extracted periodic signals, which is obtained by superimposing the extracted periodic signals, and calculating similarity between the reference signal and the extracted periodic signals, the bio-signal quality assessment apparatus 100 may select a periodic signal having a similarity value equal to or lower than a predetermined threshold value (e.g., R=0.6) from among the calculated similarities R1, R2, . . . , and Rn, and may calculate the similarity by removing only the selected periodic signal.

As described above, by calculating similarity by removing only an irregular signal, caused by arrhythmia, motion noise, or the like, from the obtained bio-signal, there is no need to re-obtain a bio-signal unnecessarily, such that the bio-signal quality assessment apparatus 100 may obtain a prompt result in response to a user's request for bio-signal quality assessment, and reliability of the quality assessment of the obtained bio-signal may be guaranteed.

However, this is merely an example of the bio-signal quality assessment apparatus 100, and instead of removing only the periodic signal occurring irregularly from the obtained bio-signal, the bio-signal quality assessment apparatus 100 may re-obtain a bio-signal, or may re-determine a signal analysis period in the obtained bio-signal to calculate similarity.

In addition, the bio-signal quality assessment apparatus 100 may calculate the signal quality index based on at least one of the following: a combination of two or more K-adjacent similarities having different K values; and statistical information of calculated similarities between the periodic signals.

For example, in the case where K values are I and J (I≠J), the bio-signal quality assessment apparatus 100 may calculate the signal quality index (SQI) by respectively calculating I-adjacent similarities RI1, RI2, . . . , and Rin, and J-adjacent similarities RJ1, RJ2, . . . , and RJn, and by combining statistics (e.g., average) of the I-adjacent similarities and the J-adjacent similarities. For example, the bio-signal quality assessment apparatus 100 may calculate, as the signal quality index (SQI), a value obtained by multiplying the I-adjacent similarities RI1, RI2, . . . , and Rin and the J-adjacent similarities RJ1, RJ2, . . . , and RJn. In this manner, by combining K-adjacent similarities having different K values, the bio-signal quality assessment apparatus 100 may assess the quality of a bio-signal more clearly.

For example, by comparing a case where an average of the I-adjacent similarities is 0.9 and an average of the J-adjacent similarities is 0.8 with a case where an average of the I-adjacent similarities is multiplied with an average of the J-adjacent similarities (e.g., combined similarity of 0.72), the bio-signal quality assessment apparatus 100 may more clearly determine whether the periodic signals of the obtained bio-signal have a similar waveform in the signal analysis period.

The bio-signal quality assessment apparatus 100 may calculate the signal quality index based on statistical information of the calculated similarities between the periodic signals extracted from the obtained bio-signal and/or a combination of the similarities.

For example, in the case of calculating similarities R1, R2, . . . , and Rn by comparing the reference signal with each of the extracted periodic signals, the bio-signal quality assessment apparatus 100 calculates an average (R1+R2+ . . . +Rn)/n) of the calculated similarities, and may determine the signal quality index (SQI) based on the average value of the calculated similarities.

In another example, the bio-signal quality assessment apparatus 100 may calculate the signal quality index (SQI) based on a combination of two or more K-adjacent similarities having different K values. For example, the bio-signal quality assessment apparatus 100 may multiply (e.g., multiply an average value of 1-adjacent similarities and an average value of M/2-adjacent similarities, where M is the number of extracted periodic signals), add, or divide average values of two or more K-adjacent similarities having different K values, or may apply the average values to a function, and may determine a value obtained as a result of the calculation to be the signal quality index (SQI).

Figure 8:
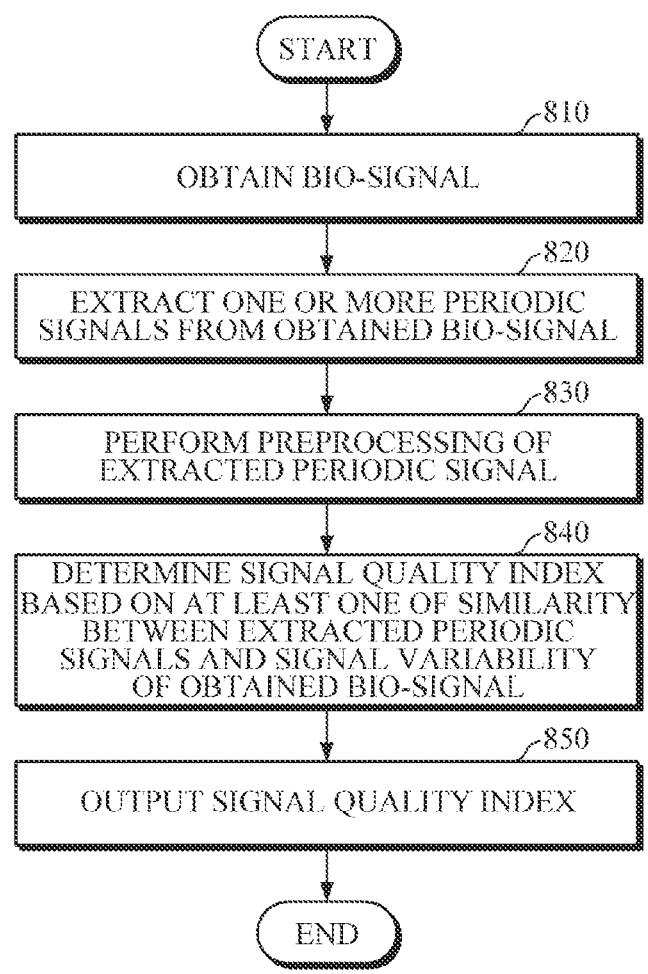
FIG. 8 is a flowchart illustrating a bio-signal quality assessment method according to another exemplary embodiment.

FIG. 8 is a flowchart illustrating a bio-signal quality assessment method according to another exemplary embodiment. The bio-signal quality assessment method of FIG. 8 may be performed by the bio-signal quality assessment apparatuses 100 and 600 illustrated in FIG. 1 and/or FIG. 6.

Referring to FIGS. 6 and 8, the bio-signal quality assessment apparatus 600 may obtain a bio-signal in operation 810.

For example, the bio-signal quality assessment apparatus 600 may measure and/or obtain the bio-signal through a sensor for measuring a bio-signal and/or a communication module for receiving a bio-signal.

Upon obtaining the bio-signal, the bio-signal quality assessment apparatus 600 may extract one or more periodic signals from the obtained bio-signal in operation 820.

For example, in the case where the obtained bio-signal is a bio-signal having periodicity, the bio-signal quality assessment apparatus 600 may extract periodic signals from the obtained bio-signal by segmenting the bio-signal in units of one period.

The bio-signal quality assessment apparatus 600 may perform preprocessing of the extracted periodic signals in operation 830.

For example, in the case where at least one of the extracted periodic signals has a different duration from other periodic signals, the bio-signal quality assessment apparatus 600 may perform preprocessing of the extracted periodic signals to calculate similarity between the extracted periodic signals.

Hereinafter, for convenience of explanation, the above explanation is described based on an example where the bio-signal quality assessment apparatus 600 performs preprocessing of the extracted periodic signals in the case where at least one of the extracted periodic signals has a different duration from other periodic signals. However, the preprocessing is not limited thereto, and the bio-signal quality assessment apparatus 600 may perform preprocessing of the extracted periodic signals if the preprocessing is required (e.g., alignment of signals, etc.) in order to calculate similarity between the extracted periodic signals.

For example, in the case where at least one of the extracted periodic signals has a different length and/or duration from other periodic signals, the bio-signal quality assessment apparatus 600 may perform preprocessing by resampling each of the extracted periodic signal so that the extracted periodic signals may have a predetermined number of samples N. To this end, the bio-signal quality assessment apparatus 600 may perform resampling of each of the extracted periodic signals by appropriately adjusting a sampling rate.

In another example, the bio-signal quality assessment apparatus 600 may determine a similarity evaluation period in each of the extracted periodic signals, and may calculate similarity between the periodic signals in the determined similarity evaluation period. For example, in the case where at least one of the extracted periodic signals has a different length and/or duration from other periodic signals, the bio-signal quality assessment apparatus 600 may extract some portion (e.g., initial 30 samples of each periodic signal, etc.) of each periodic signal, and may determine the extracted portion as the similarity evaluation period.

Upon preprocessing the extracted periodic signals, the bio-signal quality assessment apparatus 600 may calculate a signal quality index based on at least one of similarity between the extracted periodic signals and signal variability of the obtained bio-signal in operation 840.

For example, the bio-signal quality assessment apparatus 600 may calculate similarity between the extracted periodic signals and at least one of a K-adjacent periodic signal and a reference signal for each of the periodic signals.

In addition, the bio-signal quality assessment apparatus 600 may determine any one of the extracted periodic signals to be the reference signal, or may determine an average signal (e.g., ensemble average) of the extracted periodic signals, which is obtained by superimposing the extracted periodic signals, to be the reference signal.

Upon determining the reference signal, the bio-signal quality assessment apparatus 600 may calculate similarity by comparing the determined reference signal with each of the periodic signals extracted from the obtained bio-signal.

In addition, the bio-signal quality assessment apparatus 600 may determine, as similarity between periodic signals of the obtained bio-signal, statistical information (e.g., an average, a standard deviation, etc.) of a plurality of similarities R1, R2, . . . , and Rn which are calculated by comparing the determined reference signal with each of the periodic signals extracted from the obtained bio-signal.

Further, the bio-signal quality assessment apparatus 600 may calculate the signal quality index based on at least one of a combination of two or more K-adjacent similarities having different K values, and statistical information of the calculated similarities between the periodic signals.

For example, the bio-signal quality assessment apparatus 600 may calculate the signal quality index based on statistical information of the calculated similarities between the periodic signals extracted from the obtained bio-signal, and/or a combination of the similarities.

In another example, the bio-signal quality assessment apparatus 600 may calculate the signal quality index based on a combination of two or more K-adjacent similarities having different K values.

The bio-signal quality assessment apparatus 600 may output the calculated signal quality index in operation 850.

For example, the bio-signal quality assessment apparatus 600 may output at least one of the obtained bio-signal, the extracted periodic signals, the similarity evaluation period, the signal analysis period, the similarity between the periodic signals, the reference signal, the signal variability, and the signal quality index.

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A bio-signal quality assessment apparatus, comprising:
    a bio-signal obtainer configured to obtain a bio-signal; and
    a processor configured to extract periodic signals from the obtained bio-signal, determine time variability of the bio-signal based on a difference between a time duration of each of the periodic signals and an average time duration of the periodic signals, and determine a signal quality index based on the time variability and a combination of two or more K-adjacent similarities having different K distance values between the extracted periodic signals which are apart from each other.

2. The apparatus of claim 1, wherein the processor is further configured to determine a similarity evaluation period in each of the extracted periodic signals, and calculate the two or more K-adjacent similarities in the determined similarity evaluation period.

3. The apparatus of claim 1, wherein the extracted periodic signals are apart from each other by a predetermined distance.

4. The apparatus of claim 3, wherein the processor is further configured to calculate the two or more K-adjacent similarities between each of K extracted period signals, among the extracted periodic signals, and a reference signal, and determine, as the reference signal, an average signal of the extracted periodic signals which is obtained by superimposing the extracted periodic signals.

5. The apparatus of claim 3, wherein the processor is further configured to determine the signal quality index based on statistical information of the two or more K-adjacent similarities.

6. The apparatus of claim 1, wherein the processor is further configured to determine a signal analysis period so that at least one of the periodic signals is to be included.

7. The apparatus of claim 1, wherein the processor is further configured to calculate amplitude variability of the bio-signal, and determines the signal quality index based on the amplitude variability, the time variability, and the two or more K-adjacent similarities.

8. The apparatus of claim 7, wherein the processor is further configured to calculate a standard deviation or a coefficient of variation of at least one of amplitudes and durations of the extracted periodic signals and calculate the signal quality index based on the calculated standard deviation or the calculated coefficient of variation.

9. The apparatus of claim 7, further comprising an output interface configured to output at least one of the obtained bio-signal, the extracted periodic signals, a similarity evaluation period, a signal analysis period, a reference signal, the similarity between the periodic signals, the amplitude variability, the time variability, and the signal quality index.

10. A bio-signal quality assessment method, comprising:
    obtaining a bio-signal;
    extracting periodic signals from the obtained bio-signal;
    determining time variability of the bio-signal based on a difference between a time duration of each of the periodic signals and an average time duration of the periodic signals; and
    determining a signal quality index based on the time variability and a combination of two or more K-adjacent similarities having different K distance values between the extracted periodic signals which are apart from each other.

11. The method of claim 10, wherein the preprocessing comprises determining a similarity evaluation period in each of the extracted periodic signals, and calculating the two or more K-adjacent similarities in the determined similarity evaluation period.

12. The method of claim 10, wherein the extracted periodic signals which are apart from each other by a predetermined distance.

13. The method of claim 12, wherein the determining the signal quality index further comprises calculating the two or more K-adjacent similarities between each of K extracted period signals, among the extracted periodic signals, and a reference signal, and the calculating the similarity further comprises determining, as the reference signal, an average signal of the extracted periodic signals which is obtained by superimposing the extracted periodic signals.

14. The method of claim 10, wherein the determining the signal quality index comprises determining the signal quality index by calculating amplitude variability of the biosignal, and determining the signal quality index based on the amplitude variability, the time variability, and the two or more K-adjacent similarities.

15. The method of claim 14, wherein the determining the signal quality index comprises:
- determining a standard deviation or a coefficient of variation of at least one of amplitudes and durations of the extracted periodic signals; and
- determining the signal quality index based on the determined standard deviation or the determined coefficient of variation.

* * * * *